United States Patent [19]

Hefner, Jr.

[11] Patent Number: 4,559,399
[45] Date of Patent: Dec. 17, 1985

[54] POLYMER MODIFIED CYANATE AND/OR CYANAMIDE COMPOSITIONS

[75] Inventor: Robert E. Hefner, Jr., Lake Jackson, Tex.

[73] Assignee: The Dow Chemical Company, Midland, Mich.

[21] Appl. No.: 710,210

[22] Filed: Mar. 11, 1985

Related U.S. Application Data

[63] Continuation-in-part of Ser. No. 652,984, Sep. 21, 1984, abandoned.

[51] Int. Cl.$^4$ .................. C08G 59/40; C08G 73/06
[52] U.S. Cl. ........................ 528/120; 525/328.2; 525/377; 525/502; 525/534; 528/99; 528/109; 528/118; 528/363; 528/392
[58] Field of Search .............. 525/328.2, 377, 502, 525/534; 528/99, 109, 118, 120, 363, 392

[56] References Cited

U.S. PATENT DOCUMENTS

| 3,876,607 | 4/1975 | Snell et al. ................. 528/99 X |
| 4,094,852 | 6/1978 | Sundermann et al. ........... 260/37 N |
| 4,116,946 | 9/1978 | Jakob et al. ................ 528/172 |
| 4,371,689 | 2/1983 | Gaku et al. ................. 528/162 |
| 4,373,086 | 2/1983 | Ikeguchi .................... 528/363 X |
| 4,393,195 | 7/1983 | Gaku et al. ................. 528/117 X |
| 4,401,777 | 8/1983 | Tsuboi et al. ............... 528/117 X |
| 4,477,629 | 10/1984 | Hefner ..................... 528/99 X |

Primary Examiner—Earl Nielsen
Attorney, Agent, or Firm—James G. Carter

[57] ABSTRACT

A curable composition is prepared by reacting (1) an alkenylphenyl cyanate or mixture thereof, (2) an aromatic polycyanate, polycyanamide or mixture thereof and (3) a polymerizable ethylenically unsaturated material or mixture of such materials. Said curable compositions provide polymeric (cured) compositions with improved mechanical strength relative to cured aromatic polycyanates and/or polycyanamides.

18 Claims, No Drawings

POLYMER MODIFIED CYANATE AND/OR CYANAMIDE COMPOSITIONS

CROSS REFERENCE TO RELATED APPLICATION

This is a continuation-in-part application of my copending application Ser. No. 652,984 filed Sept. 21, 1984, and now abandoned.

BACKGROUND OF THE INVENTION

This invention pertains to thermosettable resin compositions having improved mechanical properties.

Resins containing the cyanate group or the cyanamide group are known and are thermosettable to polytriazines. Said polytriazines have excellent heat resistance, however, there is substantial room for improvement in their mechanical properties. U.S. Pat. No. 4,094,852 teaches the use of high boiling esters as plasticizers in cyanate resins. Although said esters improve some mechanical properties, they are not chemically bonded to the thermoset resin and may thus be easily leached out of the resin resulting in a decrease in mechanical properties.

The present invention provides novel cyanate resin compositions and novel cyanamide resin compositions which are thermosettable to useful polymeric (cured) compositions with improved mechanical strength. These compositions are useful in the preparation of castings, laminates or composites, coatings, and the like.

SUMMARY OF THE INVENTION

The present invention concerns a composition which comprises: (A) from about 0.1 to about 50, preferably from about 0.5 to about 10, most preferably from about 1 to about 5, percent by weight (pbw) of an alkenylphenyl cyanate or a mixture of alkenylphenyl cyanates represented by the formula

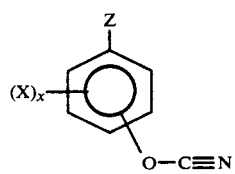
(I)

wherein Z is a

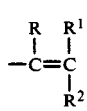

or

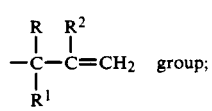

each R, R$^1$ and R$^2$ is independently hydrogen or a hydrocarbyl group having from 1 to about 3 carbon atoms; each X is independently hydrogen, a hydrocarbyl or hydrocarbyloxy group having from 1 to about 4 carbon atoms, chlorine, bromine, or a phenyl group; x has a value of 4; and (B) from 10 to about 99, preferably from about 50 to about 95, most preferably from about 75 to about 90, pbw of an aromatic polycyanate, an aromatic polycyanamide or mixtures thereof represented by the formulas

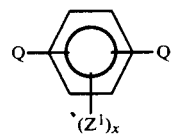
(II)

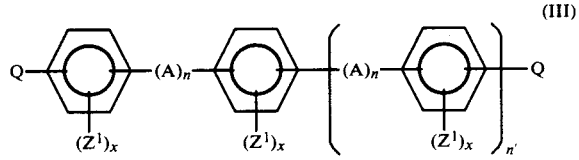
(III)

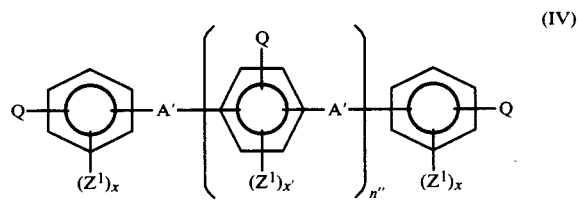
(IV)

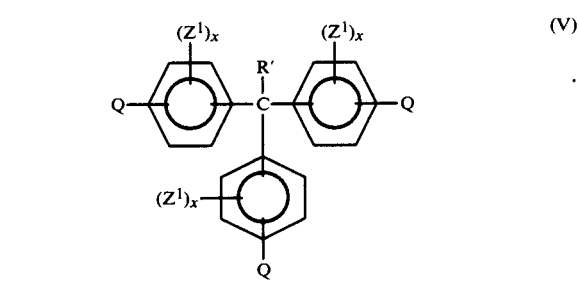
(V)

wherein each Q is independently a —O—C≡N or

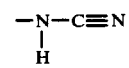

group; each A is independently a divalent hydrocarbon group having from 1 to about 10 carbon atoms, preferably from 1 to about 4 carbon atoms $$-O-,\ -\overset{O}{\underset{\|}{C}}-,\ -S-,\ -S-S-,\ -\overset{O}{\underset{\|}{S}}-,\ -\overset{O}{\underset{\underset{\|}{O}}{\overset{\|}{S}}}-\ \text{or}$$

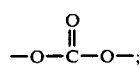

each A' is independently a divalent hydrocarbon group having from 1 to about 6, preferably from 1 to about 4 carbon atoms or a

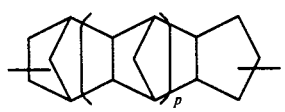

group; p has a value of from zero to about 10, preferably from zero to 3; each R' is independently hydrogen, a hydrocarbyl or hydrocarbyloxy group having from 1 to about 10, preferably from 1 to about 4 carbon atoms or a halogen, preferably chlorine or bromine; each $Z^1$ is independently hydrogen, a hydrocarbyl or hydrocarbyloxy group having from 1 to about 6 carbon atoms, chlorine, bromine, a —O—C≡N group or a

group; n has a value of zero or 1; n' has a value from zero to about 100, preferably from zero to about 10; n" has a value of from about 0.001 to about 6, preferably from about 0.01 to about 3; x has a value of 4, and x' has a value of 3; and (C) from 1 to about 50, preferably from about 5 to about 25, most preferably from about 10 to about 20, pbw of a polymerizable ethylenically unsaturated material or mixture of polymerizable ethylenically unsaturated materials and wherein the pbw of the individual components is based upon total composition.

DETAILED DESCRIPTION OF THE INVENTION

The alkenylphenyl cyanates employed herein which are represented by formula I are prepared by reaction of a stoichiometric quantity or a slight stoichiometric excess (up to about 20 percent excess) of a cyanogen halide and stoichiometric quantity of a base per hydroxy group with an alkenyl phenol represented by formula

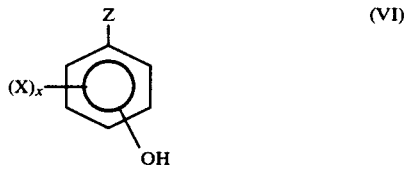

wherein Z, R, $R^1$, $R^2$, X and x are as hereinbefore defined. Suitable cyanogen halides include cyanogen bromide and cyanogen chloride. Alternately, the method of Martin and Bauer described in *Organic Synthesis*, Volume 61, pp. 35-68 (1983) and published by John Wiley and Sons can be used to generate the required cyanogen halide in situ from sodium cyanide and a halogen such as chlorine or bromine. Suitable bases include both inorganic bases and tertiary amines such as sodium hydroxide, potassium hydroxide, triethylamine, mixtures thereof and the like. Most preferred as the base is triethylamine. Suitable solvents include water, acetone, chlorinated hydrocarbons, ketones and the like. Most preferred solvents are acetone and methylene chloride. Reaction temperatures of from about —40° to about 60° C. are operable with temperatures of —20° to 25° C. being preferred.

Particularly suitable alkenylphenyl cyanates which can be employed herein include, for example, p-isopropenylphenyl cyanate, p-vinylphenyl cyanate, m-vinylphenyl cyanate, methyl-p-isopropenylphenyl cyanate, 3-chloro-4-isopropenylphenyl cyanate, p-allylphenyl cyanate, p-methallylphenyl cyanate, m-allylphenyl cyanate, 2,6-dimethyl-4-allylphenyl cyanate, mixtures thereof and the like. It is most preferred that the alkenylphenyl cyanate be substantially free of dimeric and/or oligomeric components although it is operable to use an alkenylphenyl cyanate containing substantial (up to 90 pbw) dimeric and/or oligomeric components. Said components are formed during the cyanation reaction of an alkenylphenol (VII) containing the corresponding dimeric diphenols and/or oligomeric polyphenols.

The aromatic polycyanates employed herein which are represented by formulas II, III, IV, V where Q is a —O—C≡N group are prepared by reaction of a stoichiometric or a slight stoichiometric excess (up to about 20 percent excess) of a cyanogen halide and a stoichiometric quantity of a base per hydroxyl group with an aromatic polyphenol represented by the formulas

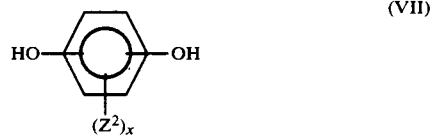

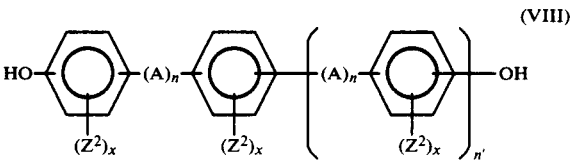

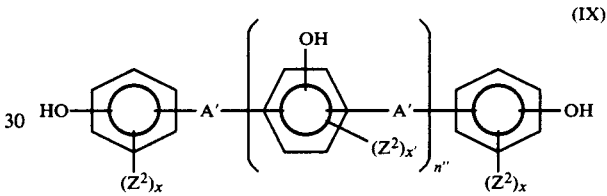

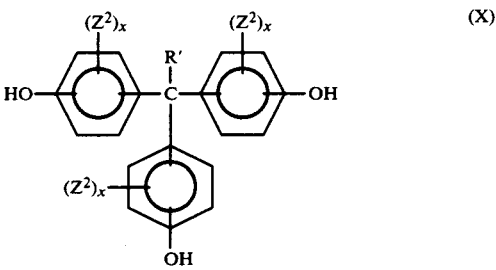

where A, A', R', n, n', n", x and x' are as hereinbefore defined and each $Z^2$ is independently hydrogen, a hydrocarbyl or hydrocarbyloxy group having from 1 to about 6 carbon atoms, chlorine, bromine or a —OH group. Suitable cyanogen halides include cyanogen bromide and cyanogen chloride. Alternately, the method of Martin and Bauer described in *Organic Synthesis*, Volume 61, pp. 35-68 (1983) and published by John Wiley and Sons can be used to generate the required cyanogen halide in situ from sodium cyanide and a halogen such as chlorine or bromine. Suitable bases include both inorganic bases and tertiary amines such as sodium hydroxide, potassium hydroxide, triethylamine, mixtures thereof and the like. Most preferred as the base is triethylamine. Suitable solvents include water, acetone, chlorinated hydrocarbons, ketones, and the like. Most preferred solvents are acetone and methylene chloride. Reaction temperatures of from about —40° to about 60° C. are operable with temperatures of —20° to 25° C. being preferred.

Particularly suitable aromatic polycyanates which can be employed herein include, for example, bisphenol A dicyanate, the dicyanates of 4,4'-dihydroxydiphenyl oxide, resorcinol, 4,4'-thiodiphenol, 4,4'-sulfonyldiphenol, 3,3',5,5'-tetrabromobisphenol A, 2,2',6,6'-tetrabromobisphenol A, 3-phenyl bisphenol A, 4,4'-dihydroxybiphenyl, 2,2'-dihydroxybiphenyl, 2,2',4,4'-tetrahydroxydiphenyl methane, 2,2',6,6'-tetramethyl-3,3',5,5'-tetrabromobisphenol A, 5,5'-dimethoxybisphenol A, the bisphenol of dicyclopentadiene, (the bis(phenol) of tricyclopentadiene,

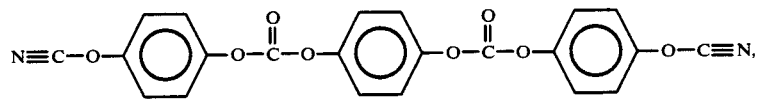

the polycyanate of a phenolformaldehyde condensation product (novolac), the polycyanate of a phenol-dicyclopentadiene condensation product and the polycyanate of 2,2',4,4'-tetrahydroxydiphenyl methane, mixtures thereof and the like.

The aromatic polycyanamides employed herein which are represented by formulas II, III, IV and V where Q is an

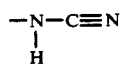

group are prepared by reaction of a stoichiometric or a slight stoichiometric excess (up to about 20 percent excess) of a cyanogen halide and a stoichiometric quantity of a base per amine group with an aromatic polyamine represented by the formulas

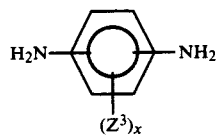
(XI)

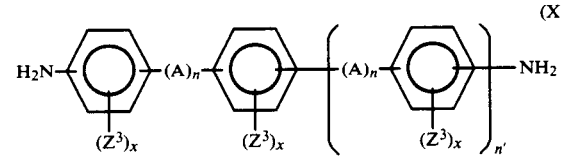
(XII)

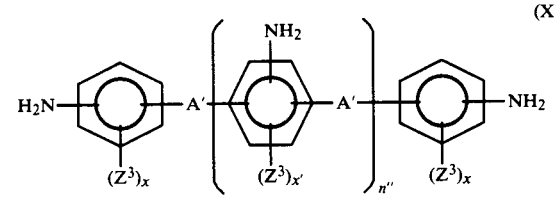
(XIII)

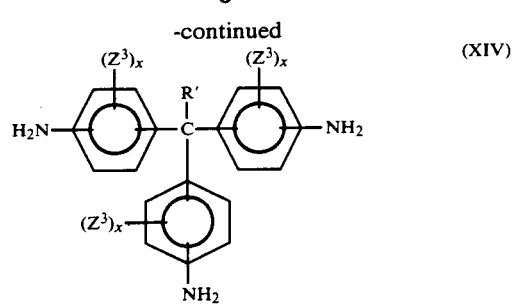
(XIV)

wherein A, A', R', n, n', n", x and x' are as hereinbefore defined and each $Z^3$ is independently hydrogen, a hydrocarbyl or hydrocarbyloxy group having from 1 to about 6 carbon atoms, chlorine, bromine or an —$NH_2$ group. The aforementioned methods used to prepare the aromatic polycyanates are generally useful for the preparation of aromatic polycyanamides.

Particularly suitable aromatic polycyanamides which can be employed herein include, for example, the dicyanamides of 4,4'-isopropylidenedianiline, 4,4'-diaminodiphenyl oxide, 1,3-diaminobenzene, 4,4'-diaminodiphenyl sulfide, 4,4'-diaminodiphenyl sulfone, 2,2',6,6'-tetrabromo-4,4'-isopropylidenedianiline, 3-phenyl-4,4'-isopropylidenedianiline, 4,4'-diaminodiphenyl, 2,2'-diaminodiphenyl, 2,2',4,4'-tetraaminodiphenyl methane, 2,2',6,6'-tetramethyl-3,3',5,5'-tetrabromo-4,4'-isopropylidenedianiline, 5,5'-dimethoxy-4,4'-isopropylidenedianiline, the dianiline of dicyclopentadiene, the dianiline of tricyclopentadiene,

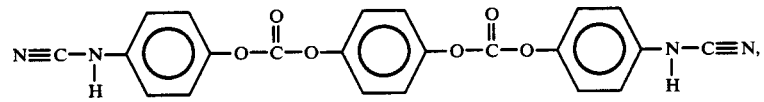

the polycyanamide of an aniline-formaldehyde condensation product, the polycyanamide of an aniline-dicyclopentadiene condensation product and the polycyanamide of 2,2',4,4'-tetraaminodiphenyl methane, mixtures thereof and the like.

The polymerizable ethylenically unsaturated materials employed herein are prepared by methods well known to the skilled artisian. Most preferred as the polymerizable ethylenically unsaturated materials are the acrylate esters represented by the formula

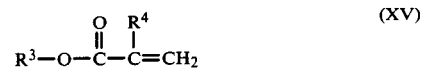
(XV)

wherein $R^3$ is a hydrocarbyl group having from 2 to about 25 carbon atoms and may be branched, cyclic or polycyclic and $R^4$ is hydrogen or a methyl group.

Typical acrylate esters represented by formula XV include ethyl acrylate, n-butyl acrylate, n-butyl methacrylate, sec-butyl acrylate, 2-ethylhexyl acrylate, 2-ethylhexyl methacrylate, n-dodecyl acrylate, cyclohexyl acrylate, methyl cyclohexyl acrylate, norbornyl acrylate, dicyclopentadiene acrylate, methyl dicyclopentadiene acrylate, mixtures thereof and the like.

Also, most preferred as the polymerizable ethylenically unsaturated materials are the vinyl aromatic compounds represented by the formula

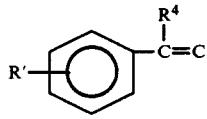

wherein R' and R⁴ are as hereinbefore defined.

Typical vinyl aromatic compounds represented by formula XVI include styrene, o-methylstyrene, m-methylstyrene, p-methylstyrene, α-methylstyrene, chlorostyrene, bromostyrene, t-butylstyrene, phenylstyrene, p-methoxystyrene, t-butyl-α-methylstyrene, mixtures thereof and the like.

Although less preferred any other of the known polymerizable ethylenically unsaturated compounds can be employed herein either alone or in any combination. Typical of these compounds are butadiene, isoprene, allylbenzene, diallylbenzene, diallylphthalate, acrylonitrile, vinyl chloride, vinyl bromide, vinyl acetate, vinyl naphthalene, the poly(ethoxy)acrylate of dicyclopentadiene, mixtures thereof and the like.

Compositions which comprise an alkenylphenyl cyanate (formula I), an aromatic polycyanate (formulas II, II, IV, V where Q=—O—C≡N) and/or an aromatic polycyanamide (formulas II, III, IV, V where

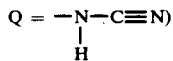

and a polymerizable ethylenically unsaturated material may be polymerized either simultaneously or in stages. In a most preferred process, an alkenylphenyl cyanate and an acrylate ester (formula XV) are first copolymerized in the presence of 0.001 to 2 percent of a suitable free radical forming catalyst and at a suitable reaction temperature while in solution in the aromatic polycyanate and/or polycyanamide. Operable free radical forming catalysts include but are not limited to the organic peroxides or hydroperoxides, persulfates, and azo or diazo compounds. Most preferred free radical forming catalysts are t-butyl peroxybenzoate, azobisisobutylronitrile, dicumylperoxide and di-t-butylperoxide. Suitable reaction temperatures are from about 65° to about 125° C. The alkenylphenyl cyanate and acrylate ester may first be mixed to form a solution which is added to the polycyanate and/or polycyanamide. Alternately, the acrylate ester may be added to a solution of the alkenylphenyl cyanate and polycyanate and/or polycyanamide. The product resulting from this copolymerization is an acrylate ester and alkenylphenyl cyanate copolymer dissolved in or mixed with a polycyanate and/or polycyanamide. This product may be cured (homopolymerized) by heating from 50° C. to 350° C. or more, preferably by heating from 70° to 200° C. and optionally in the presence of 0.001 to 5 percent of a suitable trimerization catalyst. Operable trimerization catalysts include those taught by Oehmke in U.S. Pat. No. 3,694,410 and by Sundermann, et al in U.S. Pat. No. 4,094,852. Most preferred trimerization catalysts are cobalt naphthenate and cobalt octoate. Prepolymerization (B-staging) may be affected by using lower cure temperatures and/or shorter curing times. Curing of the prepolymerized resin may then be completed at a later time or immediately following prepolymerization to comprise a single curing step.

In an alternate process, an alkenylphenyl cyanate, a polymerizable ethylenically unsaturated material and an aromatic polycyanate and/or polycyanamide are simultaneously polymerized by heating from 50° to 350° C. or more, preferably by heating from 70° to 200° C. and optionally in the presence of 0.001 to 5 percent of a suitable trimerization catalyst and, optionally, 0.001 to 2 percent of a suitable free radical forming catalyst. Operable catalysts include those previously described herein. In this process, unless the polymerizable ethylenically unsaturated material boils at a temperature substantially above that of the polymerization temperature, it can volatilize thus inducing bubbles in the polymeric product.

In a further, although less preferred, process of the invention, an alkenylphenyl cyanate and a polymerizable ethylenically unsaturated material are copolymerized in the presence of a suitable quantity, usually from about 0.001 to about 5 percent, of a free radical forming catalyst and at a suitable reaction temperature, usually from about 65° C. to about 140° C. The resulting alkenylphenyl cyanate and polymerizable ethylenically unsaturated material copolymer is then added to the polycyanate and/or polycyanamide. This product may be cured (homopolymerized) as previously described.

The cured (homopolymerized) products are polytriazines containing the copolymer of a polymerizable ethylenically unsaturated material and an alkenylphenyl cyanate. Depending on the amounts and types of alkenylphenyl cyanate and polymerizable ethylenically unsaturated material used, lesser amounts of homopolymer of the polymerizable ethylenically unsaturated material may also be present. The copolymer of the polymerizable ethylenically unsaturated material and an alkenylphenyl cyanate is chemically linked to the polytriazine structure via the triazine groups of the homopolymer. It is to be understood that the term polytriazines can also include lesser amounts of other curing structures such as, for example, copolymerization products between cyanate groups and ethylenic unsaturation from any residual polymerizable ethylenically unsaturated material.

The amount of alkenylphenyl cyanate used in the composition can be varied to control whether or not the copolymer of a polymerizable ethylenically unsaturated material and an alkenylphenyl cyanate is soluble or insoluble in the homopolymerized (cured) product. Use of about 0.1 to about 2 pbw of an alkenylphenyl cyanate generally provides a polymeric product wherein the copolymer of a polymerizable ethylenically unsaturated material and an alkenylphenyl cyanate is insoluble (phased-out). Use of more than 2 to about 50 pbw of an alkenylphenyl cyanate generally provides a polymeric product wherein the copolymer of a polymerizable ethylenically unsaturated material and an alkenylphenyl cyanate is soluble (monophasic or single phase).

The polymerizable ethylenically unsaturated material and alkenylphenyl cyanate copolymer dissolved in or mixed with an aromatic polycyanate and/or polycyanamide may be mixed with a polyepoxide to form a copolymerizable (curable) mixture. Suitable polyepoxides optionally employed herein are represented by the formulas

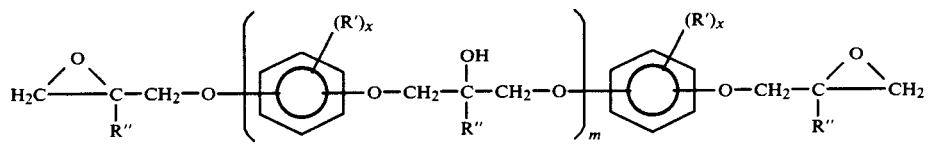

XVII.

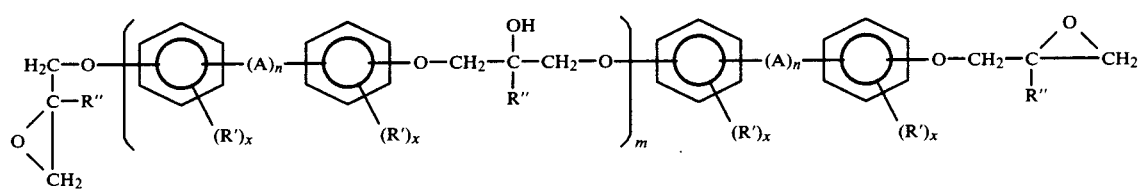

XVIII.

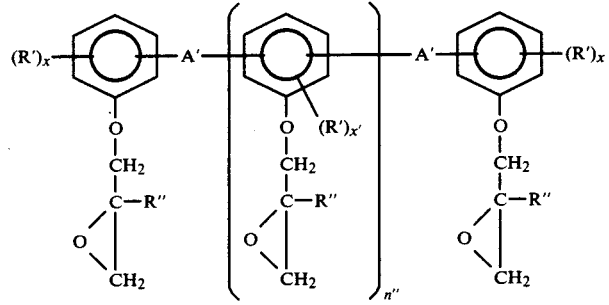

XIX.

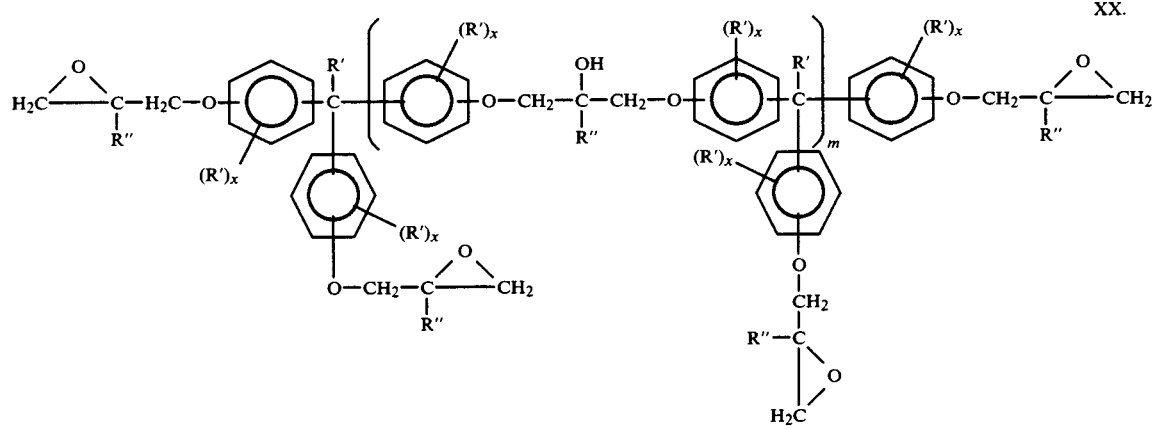

XX.

where A, A', R', n, n", x and x' are as hereinbefore defined, each R" is independently hydrogen or an alkyl group having from 1 to about 4 carbon atoms and m has a value of from about zero to about 30, preferably from about zero to about 5.

Particularly suitable polyepoxides which can be employed herein include, for example, the diglycidyl ethers of resorcinol, bisphenol A, 3,3',5,5'-tetrabromobisphenol A, the triglycicyl ether of tris(hydroxyphenyl)methane, the polyglycidyl ether of a phenol-formaldehyde condensation product (novolac), the polyglycidyl ether of a dicyclopentadiene and phenol condensation product and the like. The polyepoxides can be used either alone or in combination.

The aforementioned polyepoxides represented by formulas XVI, XVII, XVIII and XIX can be prepared by reaction of a diphenol or polyphenol represented by formulas VIII, IX, X and XI with an epihalohydrin and a basic acting material. Said reaction generally involves two distinct steps: coupling reaction of the epihalohydrin and diphenol or polyphenol to provide a halohydrin intermediate and dehydrohalogenation reaction of the halohydrin intermediate to provide the glycidyl ether product. Suitable catalysts and reaction conditions for preparing polyepoxides are described in the *Handbook of Epoxy Resins* by Lee and Neville, McGraw-Hill (1967) and in U.S. Pat. Nos. 3,948,855 and 3,477,990 which are incorporated herein by reference.

Curing of the polymerizable ethylenically unsaturated material and alkenylphenyl cyanate copolymer dissolved in or mixed with an aromatic polycyanate and/or polycyanamide and polyepoxide mixture is accomplished using the methods previously described for curing of the polymerizable ethylenically unsaturated material and alkenylphenyl cyanate dissolved in or mixed with an aromatic polycyanate and/or polycyanamide.

The compositions of the present invention are useful in the preparation of castings, laminates or composites, coatings and the like, especially where high mechanical strength or toughness are desired.

In the preparation of laminates or composites from the compositions of the present invention, suitable substrates include, but are not limited to, woven and non-woven fibers and/or filaments of glass, carbon, graphite, boron, aramid, asbestos, glass and carbon hybrids, combinations thereof and the like.

EXAMPLE 1

A. Preparation of p-Isopropenylphenyl Cyanate

A 134.17 gram (1.00 mole) portion of p-isopropenyl phenol, 111.23 grams (1.05 mole) of cyanogen bromide and 600 milliliters of acetone were added to a reactor and maintained under a nitrogen atmosphere with stirring. The p-isopropenyl phenol used herein was of in excess of 99 percent purity. The stirred solution was cooled to −10° C. then 101.19 grams (1.00 mole) of triethylamine was added to the reactor over a twenty minute (1200 s) period and so as to maintain the reaction temperature of −5° to −2° C. After completion of the triethylamine addition, the reactor was maintained at −2° to 5° C. for an additional thirty minutes (1800 s), followed by addition of the reactor contents to 1 gallon (3.97 l) of chilled deionized water. After five minutes (300 s) the water and product mixture was multiply extracted with three 400 milliliter volumes of methylene chloride. The combined methylene chloride extract was washed with 500 milliliters of 5 percent aqueous hydrochloric acid followed by washing with 800 milliliters of deionized water then drying over anhydrous sodium sulfate. The dry methylene chloride extract was filtered and solvent removed by rotary evaporation under vacuum. p-Isopropenylphenyl cyanate (132.5 grams) was recovered in 83.2 percent yield as a transparent light amber colored liquid. Infrared spectrophotometric analysis of a film sample of the product confirmed the product structure (disappearance of phenolic hydroxyl group, appearance of —C≡N group). Gas chromatographic-mass spectroscopic analysis of the product confirmed the structure for p-isopropenylphenyl cyanate (parent ion m/e=159) with essentially no other compounds being present.

B. Preparation of Bisphenol A Dicyanate

A 342.45 gram (1.50 moles) portion of 4,4'-isopropylidenediphenol, 333.68 grams (3.15 moles) of cyanogen bromide and 1000 milliliters of acetone were added to a reactor and maintained under a nitrogen atmosphere with stirring. The stirred solution was cooled to −5° C. then 305.09 grams (3.015 moles) of triethylamine was added to the reactor over a twenty-five minute (1500 s) period and so as to maintain the reaction temperature at −5° to 0° C. After completion of the triethylamine addition, the reactor was maintained at −2° to 5° C. for an additional 50 minutes (3000 s), followed by addition of the reactor contents to 1 gallon (3.79 l) of chilled deionized water. After 5 minutes (300 s) the water and product mixture was extracted with three 500 milliliter portions of methylene chloride. The combined methylene chloride extract was washed with 500 milliliters of 5 percent aqueous hydrochloric acid followed by washing with 800 milliliters of deionized water then drying over anhydrous sodium sulfate. The dry methylene chloride solution was filtered and solvent removed by rotary evaporation under vacuum. Bisphenol A dicyanate (360.7 grams) was recovered in 86.4 percent yield as a white crystalline solid. Infrared spectrophotometric analysis of a film sample of the product confirmed the product structure (disappearance of phenolic hydroxyl group, appearance of —C≡N group).

C. Copolymerization of 2-Ethylhexyl Acrylate and p-Isopropenylphenyl Cyanate in a Bisphenol A Dicyanate Solution A 189.0 gram (84.0 percent by weight, bpw) portion of bisphenol A dicyanate prepared in B above and a 2.25 gram (1.0 pbw) portion of p-isopropenylphenyl cyanate prepared in A above were added to a reactor and maintained under a nitrogen atmosphere. The reactor contents were heated to a 110° C. solution then stirring commenced and 0.45 gram of azobisisobutyronitrile was added. Two minutes (120 s) later, dropwise addition of 33.75 grams (15.0 pbw) of 2-ethylhexyl acrylate commenced and was completed over a twenty minute (1200 s) period. After an additional 60 minutes (3600) of reaction at the 110° C. reaction temperature, the product was rotary evaporated under vacuum for 60 minutes (3600 s) at 100° C. The copoly(2-ethylhexyl acrylate and p-isopropenylphenyl cyanate) in bisphenol A dicyanate was recovered (225.2 grams) in essentially quantitative yield as a transparent light amber colored solution.

D. Polymerization of Copoly(2-Ethylhexyl Acrylate and p-Isopropenylphenyl Cyanate) in Bisphenol A Dicyanate Solution A 216.7 gram portion of copoly(2-ethylhexyl acrylate and p-isopropenylphenyl cyanate) in bisphenol A dicyanate was heated to 60° C. and 0.22 gram of cobalt naphthenate (6.0 percent active) was added. This solution was poured into a ⅛ inch (3.175 mm) mold made from a pair of glass plates and then placed in an oven and maintained at 125° C. for 2 hours (7200 s) then 177° C. for 2 hours (7200 s). The opaque light green colored, unfilled casting was demolded and used to prepare test pieces for tensile and flexural strength, flexural modulus, percent elongation and average Barcol Hardness (934-1 scale) determinations. Mechanical properties of tensile (6) and flexural (6) test pieces were determined using an Instron machine with standard test methods (ASTM D-638 and D-790). The results are reported in Table I.

TABLE I

| | |
|---|---|
| Barcol Hardness | 34 |
| Tensile Strength, psi/kPa | 7,252/50,001 |
| Elongation (%) | 2.30 |
| Flexural Strength, psi/kPa | 11,614/80,076 |
| Flexural Modulus, psi/kPa | 450,000/3,102,660 |

COMPARATIVE EXPERIMENT A

Polymerization of Bisphenol A Dicyanate

A 161.3 gram portion of bisphenol A dicyanate prepared in Example 1-B was heated to 60° C. and 0.16 gram of cobalt naphthenate (6.0 percent active) was added. This solution was used to prepare a clear unfilled ⅛ inch (3.175 mm) casting using the method of Example 1-D. The mechanical properties of the transparent, light amber colored, clear unfilled casting were determined using the method of Example 1-D. The results are reported in Table II.

TABLE II

| | |
|---|---|
| Barcol Hardness | 48 |
| Tensile Strength, psi/kPa | 7,258/50,042 |
| Elongation (%) | 1.42 |
| Flexural Strength, psi/kPa | 11,727/80,855 |
| Flexural Modulus, psi/kPa | 660,000/4,550,568 |

EXAMPLE 2

A. Copolymerization of 2-Ethylhexyl Acrylate and p-Isopropenylphenyl Cyanate in a Bisphenol A Dicyanate Solution A 173.7 gram (80.0 percent by weight, pbw) portion of Bisphenol A dicyanate prepared using the method of Example 1-B and a 10.86 gram (5.0 pbw) portion of p-isopropenylphenyl cyanate prepared in Example 1-A were added to a reactor and maintained under a nitrogen atmosphere. The reactor contents were heated to a 110° C. solution then stirring commenced and 0.43 gram of azobisisobutyronitrile was added. Two minutes (120 s) later, dropwise addition of 32.57 grams (15.0 pbw) of 2-ethylhexyl acrylate commenced and was completed over a twenty minute (1200 s) period. After an additional 60 minutes (3600 s) of reaction at the 110° C. reaction temperature, the product was rotary evaporated under vacuum for 60 minutes (3600 s) at 100° C. The copoly(2-ethylhexyl acrylate and p-isopropenylphenyl cyanate) in bisphenol A dicyanate was recovered (216.9 grams) in essentially quantitative yield as a transparent light amber colored solution.

B. Polymerization of Copoly(2-Ethylhexyl Acrylate and p-Isopropenylphenyl Cyanate) in Bisphenol A Dicyanate Solution A 212.0 gram portion of copoly(2-ethylhexyl acrylate and p-isopropenylphenyl cyanate) in bisphenol A dicyanate was heated to 60° C. and 0.21 gram of cobalt naphthenate (6.0 percent active) was added. This solution was poured into a ⅛ inch (3.175 mm) mold made from a pair of glass plates and then placed in an oven and maintained at 125° C. for 2 hours (7200 s) then 177° C. for 2 hours (7200 s). The transparent, light amber colored, clear unfilled casting was demolded and used to prepare test pieces which were evaluated using the method of Example 1-D. The results are reported in Table III.

TABLE III

| | |
|---|---|
| Barcol Hardness | 43 |
| Tensile Strength, psi/kPa | 12,328/84,999 |
| Elongation (%) | 4.28 |
| Flexural Strength, psi/kPa | 22,383/154,326 |
| Flexural Modulus, psi/kPa | 522,000/3,599,086 |

EXAMPLE 3

A. Copolymerization of 2-Ethylhexyl Acrylate and p-Isopropenylphenyl Cyanate in a Bisphenol A Dicyanate Solution A 173.7 gram (80.0 percent by weight, pbw) portion of Bisphenol A dicyanate prepared using the method of Example I-B was added to a reactor and maintained under a nitrogen atmosphere. The reactor contents were heated to a 95° C. solution then stirring commenced and 0.43 gram of azobisisobutyronitrile was added. Two minutes (120 s) later, dropwise addition of 32.57 grams (15.0 pbw) of 2-ethylhexyl acrylate and 10.86 grams (5.0 pbw) of p-isopropenylphenyl cyanate as a mixture commenced and was completed over a twenty minute (1200 s) period. After an additional 90 minutes (5400 s) of reaction at the 95° C. reaction temperature, the product was rotary evaporated under vacuum for 30 minutes (1800 s) at 100° C. The copoly(2-ethylhexyl acrylate and p-isopropenylphenyl cyanate) in bisphenol A dicyanate was recovered in essentially quantitative yield as a transparent light amber colored solution.

B. Polymerization of Copoly(2-Ethylhexyl Acrylate and p-Isopropenylphenyl Cyanate) in Bisphenol A Dicyanate Solution A 210.0 gram portion of copoly(2-ethylhexyl acrylate and p-isopropenylphenyl cyanate) in bisphenol A dicyanate was heated to 60° C. and 0.21 grams of cobalt naphthenate (6.0 percent active) was added. This solution was poured into a ⅛ inch (3.175 mm) mold made from a pair of glass plates and then placed in an oven and maintained at 125° C. for 2 hours (7200 s) then 177° C. for 2 hours (7200 s). The transparent, light amber colored, clear unfilled casting was demolded and used to prepare test pieces which were evaluated using the method of Example I-D. The results are reported in Table IV.

TABLE IV

| | |
|---|---|
| Barcol Hardness | 33 |
| Tensile Strength, psi/kPa | 9236/63,680 |
| Elongation (%) | 2.41 |
| Flexural Strength, psi/kPa | 14,998/103,408 |
| Flexural Modulus, psi/kPa | 497,000/3,426,716 |

EXAMPLE 4

Portions (0.2 grams) of the copoly(2-ethylhexyl acrylate and p-isopropenylphenyl cyanate) in bisphenol A dicyanate solutions from Example 1-C, Example 2-A and Example 3-A were analyzed by gel permeation chromatography using polystyrene standards. The weight average molecular weight and polydispersity ratio of the 2-ethylhexyl acrylate and p-isopropenylphenyl cyanate copolymer portion of each of the respective solutions are reported in Table V.

TABLE V

| | Weight Average Molecular Weight | Polydispersity Ratio |
|---|---|---|
| Example 1-C | 1004 | 1.18 |
| Example 2-A | 843 | 1.18 |
| Example 3-A | 2146 | 1.78 |

EXAMPLE 5

Portions of the clear, unfilled castings of Example 1-D, Example 2-B and Comparative Experiment A were analyzed by differential scanning calorimetry (DSC) under a nitrogen atmosphere and at a scanning rate of 10° C. per minute from 30° to 450° C. The glass transition temperature (Tg) are reported in Table VI.

TABLE VI

| Sample Designation | Tg Midpoint (°C.) |
|---|---|
| Example 1-D | 137 |
| Example 2-B | 190 |
| Comparative Experiment A | 179 |

EXAMPLE 6

Portions of the clear, unfilled castings of Example 1-D, Example 2-B and Comparative Experiment A were analyzed by thermogravimetric analysis (TGA). Weight loss was recorded as a function of temperature at a 10° C. per minute rate of increase in a stream of nitrogen flowing at 35 cubic centimeters per minute. The results are reported in Table VII.

TABLE VII

| Sample Designation | Weight Loss (%) | | | | | | |
|---|---|---|---|---|---|---|---|
| | 100 °C. | 300 °C. | 350 °C. | 400 °C. | 500 °C. | 700 °C. | 950 °C. |
| Example 1-D | 0.0 | 4.1 | 7.0 | 15.8 | 62.0 | 69.9 | 71.8 |
| Example 2-B | 0.0 | 1.9 | 3.6 | 7.8 | 53.0 | 63.2 | 64.0 |
| Comparative Experiment A | 0.0 | 1.6 | 6.3 | 15.5 | 52.0 | 61.5 | 63.9 |

EXAMPLE 7

A. Preparation of a Dicyclopentadiene-Phenol Addition Product

Phenol (2352.75 grams, 25.0 moles) was added to a reactor and maintained at 45° C. with stirring under a nitrogen atmosphere. A 99.2 gram portion of Filtrol 1 (an acidified clay manufactured by Filtrol Corporation) was then added to the reactor. Dicyclopentadiene (330.53 grams, 2.5 moles) was added over a 2.75 hour (9900 s) period so that the reaction temperature reached 80° C. by the end of the dicyclopentadiene addition. The reaction temperature was increased to 150° C. and maintained for 3 hours (10800 s) after which time gas chromatographic analysis of a sample of the reaction product demonstrated that 100 percent conversion of the dicyclopentadiene had occurred. The reactor was cooled to 60° C. and the Filtrol 1 removed by filtration. The filtrate was vacuum distilled reaching a maximum pot temperature of 240° C. at 20 to 0.5 mm Hg. This removed excess phenol and dicyclopentadienyl monophenols. The dicyclopentadiene-phenol addition product was recovered in 80% yield as a transparent orange-red colored solid. Gas chromatographic-mass spectroscopic analysis and infrared spectrophotometric analysis confirmed the product structure for the dicyclopentadiene-phenol addition product. Titration demonstrated the presence of 10.12 percent by weight phenolic hydroxyl groups in the product.

B. Preparation of a Polycyanate of a Dicyclopentadiene-Phenol addition product A 400.0 gram (2.381 moles of hydroxyl groups) portion of the dicyclopentadiene-phenol addition product, 264.83 grams (2.50 moles) of cyanogen bromide and 700 milliliters of acetone were added to a reactor and maintained under a nitrogen atmosphere with stirring. The stirred solution was cooled to −5° C. then 242.14 grams (2.39 moles) of triethylamine was added to the reactor over a thirty minute (1800 s) period and so as to maintain the reaction temperature of −5° to −2° C. After completion of the triethylamine addition, the reactor was maintained at −2° to 2° C. for an additional 40 minutes (2400 s), followed by addition of the reactor contents to one gallon (3.79 l) of chilled deionized water. After five minutes (300 s) the water and product mixture was multiply extracted with three 400 milliliter volumes of methylene chloride. The combined methylene chloride extract was washed with 500 milliliters of 1.5 percent aqueous hydrochloric acid followed by washing with 1000 milliliters of deionized water then drying over anhydrous sodium sulfate. The dry methylene chloride extract was filtered and solvent removed by rotary evaporation under vacuum. The polycyanate of the dicyclopentadiene-phenol addition product (438.42 grams) was recovered as a light amber colored viscous liquid. Infrared spectrophotometric analysis of a film sample of the product confirmed the product structure (disappearance of phenolic hydroxyl group, appearance of —C≡N group).

C. Copolymerization of 2-Ethylhexyl Acrylate and p-Isopropenylphenyl Cyanate in a Polycyanate of Dicyclopentadiene-Phenol addition product A 173.7 gram (80.0 percent by weight, pbw) portion of the polycyanate of dicyclopentadiene-phenol addition product prepared in A above and a 10.86 gram (5.0 pbw) portion of p-isopropenylphenyl cyanate prepared using the method of Example 1-A were added to a reactor and maintained under a nitrogen atmosphere. The reactor contents were heated to a 110° C. solution then stirring commenced and 0.43 gram of azobisisobutyronitrile was added. Two minutes (120 s) later, dropwise addition of 32.57 grams (15.0 pbw) of 2-ethylhexyl acrylate commenced and was completed over a twenty minute (1200 s) period. After an additional 60 minutes (3600 s) of reaction at the 110° C. reaction temperature, the product was rotary evaporated under vacuum for 60 minutes (3600 s) at 100° C. The copoly(2-ethylhexyl acrylate and p-isopropenylphenyl cyanate) in polycyanate of dicyclopentadiene-phenol addition product was recovered (217.0 grams) in essentially quantitative yield as a light amber colored solution.

D. Gel Permeation Chromatographic Analysis of Copoly(2-Ethylhexyl Acrylate and p-Isopropenylphenyl Cyanate) in Polycyanate of Dicyclopentadiene-Phenol addition product A portion (0.2 gram) of the copoly(2-ethylhexyl acrylate and p-isopropenylphenyl cyanate) in polycyanate of dicyclopentadiene-phenol addition product from B above was analyzed by gel permeation chromatography using polystyrene standards. The weight average molecular weight of the 2-ethyl hexyl acrylate and p-isopropenylphenyl cyanate copolymer was 1287 and the polydispersity ratio was 1.20.

EXAMPLE 8

A. Copolymerization of 2-Ethylhexyl Acrylate and p-Isopropenylphenyl Cyanate in a Polycyanate of Dicyclopentadiene-Phenol addition product A 175.0 gram (75.26 percent by weight, pbw) portion of a polycyanate of a dicyclopentadiene-phenol addition product prepared using a method similar to that of Example 7-A was added to a reactor and maintained under a nitrogen atmosphere. The reactor contents were heated to a 110° C. solution then stirring commenced and 0.575 gram of azobisisobutyronitrile was added. Two minutes (120 s) later, dropwise addition of 46.60 grams (20.04 pbw) of 2-ethylhexyl acrylate and 10.94 grams (4.70 pbw) of p-isopropenylphenyl cyanate as a mixture commenced and was completed over a twenty minute (1200 s) period. After an additional 60 minutes (3600 s) of reaction at the 110° C. reaction temperature, the product was rotary evaporated under vacuum for 15 minutes (900 s) at 100° C. The copoly(2- ethylhexyl acrylate and p-isopropenylphenyl cyanate) in polycyanate of dicyclopentadiene-phenol addition product was recovered in essentially quantitative yield as a light amber colored solution.

B. Polymerization of Copoly(2-Ethylhexyl Acrylate and p-Isopropenylphenyl Cyanate) in Polycyanate of Dicyclopentadiene-Phenol addition product Solution A 200.0 gram portion of copoly(2-ethylhexyl acrylate and p-isopropenylphenyl cyanate) in polycyanate of dicyclopentadiene-phenol addition product was heated to 60° C. and 0.20 gram of cobalt naphthenate (6.0 percent active) was added. This solution was poured into a ⅛ inch (3.175 mm) mold made from a pair of glass plates and then placed in an oven and maintained at 125° C. for 2 hours (7200 s) then 177° C. for 2 hours (7200 s). The transparent, light amber colored, clear unfilled casting was demolded and used to prepare test pieces which were evaluated using the method of Example 1-D. The results are reported in Table VIII.

TABLE VIII

| Barcol Hardness | 20 |
|---|---|
| Tensile Strength, psi/kPa | 6,806/46,926 |
| Elongation (%) | 3.68 |
| Flexural Strength, psi/kPa | 11,794/81,317 |
| Flexural Modulus, psi/kPa | 334,000/2,302,863 |

COMPARATIVE EXPERIMENT B

Polymerization of a Polycyanate of Dicyclopentadiene-Phenol addition product

A 175.0 gram portion of the polycyanate of dicyclopentadiene-phenol addition product as used in Example 8-A was heated to 6° C. and 0.175 gram of cobalt naphthenate (6.0 percent active) was added. This solution was used to prepare a clear unfilled ⅛ inch (3.175 mm) casting using the method of Example 1-D. The resulting casting could not be cut or machined to provide tensile or flexural test pieces for evaluation due to excessive chipping and fracturing.

EXAMPLE 9

A. Preparation of Copoly(2-Ethylhexyl Acrylate and p-Isopropenylphenyl Cyanate

A 5.0 gram (5.0 percent by weight, pbw) portion of p-isopropenylphenyl cyanate prepared using the method of Example 1-A and 95.0 grams (95.0 pbw) of 2-ethylhexyl acrylate were added to a reactor and maintained under a nitrogen atmosphere with stirring. The stirred solution was heated to 90° C., then 0.20 gram of azobisisobutyronitrile was added. After 40 minutes (2400 s) of reaction at the 90° C. reaction temperature, the copoly(2-ethylhexyl acrylate and p-isopropenylphenyl cyanate) was recovered as a transparent syrup-like liquid in essentially quantitative yield. Infrared spectrophotometric analysis of a film sample of the product confirmed complete retention of the —C≡N group in the product. Gel permeation chromatographic analysis of a 0.2 gram portion of the product using polystyrene standards demonstrated a pair of components present at 62 and 38 area percent with weight average molecular weights of 238 and 182,280 and with polydispersity ratios of 1.09 and 3.51, respectively. The Brookfield viscosity (25° C.) of the product was 52 cp.

B. Copolymerization of Copoly(2-Ethylhexyl Acrylate and p-Isopropenylphenyl Cyanate) with Bisphenol A Dicyanate A 40.0 gram portion of copoly(2-ethylhexyl acrylate and p-isopropenylphenyl cyanate) from A above and a 160.0 gram portion of bisphenol A dicyanate prepared using the method of Example 1-B were combined and heated to 60° C. Cobalt naphthenate (6.0 percent active, 0.20 gram) was added and the solution was poured into a ⅛ inch (3.175 mm) mold made from a pair of glass plates and then placed in an oven and maintained at 125° C. for 2 hours (7200 s) then 177° C. for 2 hours (7200 s). The opaque, light amber colored, unfilled casting was demolded and used to prepare test pieces which were evaluated using the method of Example 1-D. The results are reported in Table IX.

TABLE IX

| Barcol Hardness | 20 |
|---|---|
| Tensile Strength, psi/kPa | 6,503/44,837 |
| Elongation (%) | 2.59 |
| Flexural Strength, psi/kPa | 11,561/79,711 |
| Flexural Modulus, psi/kPa | 389,000/2,682,077 |

EXAMPLE 10

Copolymerization of Copoly(2-Ethylhexyl Acrylate and p-Isopropenylphenyl Cyanate) in Bisphenol A Dicyanate Solution with a Diglycidyl Ether of Bisphenol A A 100.0 gram portion of copoly(2-ethylhexyl acrylate and p-isopropenylphenyl cyanate in bisphenol A dicyanate prepared using the method of Example 3-A was heated to 60° C. A mixture of 0.21 gram of cobalt naphthenate (6.0 percent active) and 110.06 grams of a diglycidyl ether of bisphenol A having an epoxide equivalent weight (EEW) of 181.53 was then added and thoroughly mixed. The resulting solution was poured into a ⅛ inch (3.175 mm) mold made from a pair of glass plates and then placed in an oven and maintained at 125° C. for 2 hours (7200 s) then 177° C. for 2 hours (7200 s). The transparent, light yellow colored, clear, unfilled casting was demolded and used to prepare test pieces which were evaluated using the method of Example 1-D. Additional test pieces (2) were prepared for determination of the heat distortion temperature (264 psi) using standard test methods (ASTM D-648 modified). The results are reported in Table X.

TABLE X

| Barcol Hardness | 42 |
|---|---|
| Tensile Strength, psi/kPa | 11,426/78,780 |
| Elongation (%) | 3.34 |
| Flexural Strength, psi/kPa | 19,688/135,744 |
| Flexural Modulus, psi/kPa | 490,000/3,378,431 |
| Heat Distortion Temperature °F./°C. | 274/134.4 |

EXAMPLE 11

A. Copolymerization of Styrene and p-Isopropenylphenyl Cyanate in a Bisphenol A Dicyanate Solution A 173.7 gram (80.0 percent by weight, pbw) portion of bisphenol A dicyanate prepared using the method of Example 1-B was added to a reactor and maintained under a nitrogen atmosphere. The reactor contents were heated to a 110° C. solution then stirring commenced and addition of a solution containing 0.43 gram of azobisisobutyronitrile, styrene (32.57 grams, 15.0 pbw) and p-isopropenylphenyl cyanate (10.86 grams, 5.0 pbw) was started and was completed over a twenty minute (1200 s) period. After an additional 60 minutes (3600 s) of reaction at the 110° C. reaction temperature, the copoly(styrene and p-isopropenylphenyl cyanate) in bisphenol A dicyanate was recovered (216.7 grams) in essentially quantitative yield as a transparent, light amber colored solution.

B. Polymerization of Copoly(Styrene and p-Isopropenylphenyl Cyanate in Bisphenol A Dicyanate Solution A 200.0 gram portion of copoly(styrene and p-isopropenylphenyl cyanate in bisphenol A dicyanate was heated to 40° C. and 0.21 gram of cobalt naphthenate (6.0 percent active) was added. This solution was poured into a ⅛ inch (3.175 mm) mold made from a pair of glass plates and then placed in an oven and maintained at 125° C. for 2 hours (7200 s), 177° C. for 2 hours (7200 s) then 200° C. for 2 hours (7200 s). The transparent, light amber colored, clear, unfilled casting was demolded and used to prepare test pieces which were evaluated using the method of Example 1-D. The results are reported in Table XI.

TABLE XI

| Barcol Hardness | 45 |
| Tensile Strength, psi/kPa | 10,982/75,719 |
| Elongation (%) | 2.51 |
| Flexural Strength, psi/kPa | 17,510/120,728 |
| Flexural Modulus, psi/kPa | 636,000/4,385,093 |

I claim:
1. A composition comprising
(A) from about 0.1 to about 50 percent by weight of at least one alkenylphenyl cyanate represented by formula I in the specification;
(B) from about 10 to about 99 percent by weight of at least one aromatic polycyanate or aromatic polycyanamide or mixture thereof represented by formulas II, III, IV or V in the specification; and
(C) from 1 to about 50 percent by weight of at least one polymerizable ethylenically unsaturated material;
wherein the percent by weight of the components is based upon total weight of the components (A), (B) and (C).
2. A composition of claim 1 wherein
(i) component (A) is present in quantities of from about 0.5 to about 10 percent by weight;
(iii) component (B) is present in quantities of from about 50 to about 95 percent by weight; and
(iii) component (C) is present in quantities of from about 5 to about 25 percent by weight.
3. A composition of claim 2 wherein
(i) component (A) is present in quantities of from about 1 to about 5 percent by weight;
(ii) component (B) is present in quantities of from about 75 to about 90 percent by weight; and
(iii) component (C) is present in quantities of from about 10 to about 20 percent by weight.
4. A composition of claims 1, 2 or 3 wherein component (B) is an aromatic polycyanate or mixture of such polycyanates.
5. A composition of claim 4 wherein
(i) component (A) is p-isopropenylphenyl cyanate;
(ii) component (B) is bisphenol A dicyanate or a polycyanate of a dicyclopentadiene-phenol addition product; and
(iii) component (C) is an acrylate ester represented by formula XV in the specification of an unsaturated aromatic compound represented by formula XVI in the specification wherein R' is hydrogen, a hydrocarbyl or hydrocarbyloxy group having from 1 to about 10 carbon atoms or a halogen; $R^3$ is a hydrocarbyl group having from 2 to about 25 carbon atoms and may be branched, cyclic or polycyclic and $R^4$ is hydrogen or a methyl group.
6. A composition of claims 1, 2 or 3 wherein from about 1 to about 99 pbw of a polyepoxide represented by formulas XVII, XVIII, XIX or XX in the specification wherein each A is independently a divalent hydrocarbon group having from 1 to about 10 carbon atoms,

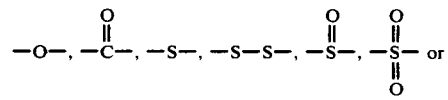

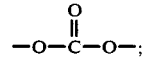

each A' is independently a divalent hydrocarbon group having from 1 to about 6 carbon atoms or a

group; p has a value of from zero to about 10; each R' is independently hydrogen, a hydrocarbyl or hydrocarbyloxy group having from 1 to about 10 carbon atoms; each R" is independently hydrogen or an alkyl group having from 1 to about 4 carbon atoms; m has a value of from about zero to about 30; n has a value of zero or 1; n" has a value of from about 0.001 to about 6; x has a value of 4 and x' has a value of 3 is present.
7. A composition of claim 6 wherein said polyepoxide is a diglycidyl ether of bisphenol A.
8. A composition of claim 4 wherein from about 10 to about 50 pbw of a polyepoxide represented by formulas XVII, XVIII, XIX or XX in the specification wherein each A is independently a divalent hydrocarbon group having from 1 to about 10 carbon atoms,

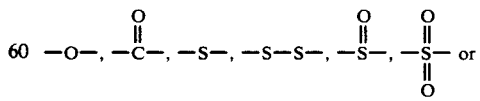

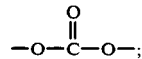

each A' is independently a divalent hydrocarbon group having from 1 to about 6 carbon atoms or a

[structure: bridged polycyclic group with subscript p]

group; p has a value of from zero to about 10; each R' is independently hydrogen, a hydrocarbyl or hydrocarbyloxy group having from 1 to about 10 carbon atoms; each R" is independently hydrogen or an alkyl group having from 1 to about 4 carbon atoms; m has a value of from about zero to about 30; n has a value of zero or 1; n" has a value of from about 0.001 to about 6; x has a value of 4 and x' has a value of 3 is present.

9. A composition of claim 6 wherein said polyepoxide is a diglycidyl ether of bisphenol A.

10. A product resulting from curing a composition of claims 1, 2 or 3.

11. A product resulting from curing a composition of claim 4.

12. A product resulting from curing a composition of claim 5.

13. A product resulting from curing a composition of claim 6.

14. A product resulting from curing a composition of claim 7.

15. A product resulting from curing a composition of claim 8.

16. A product resulting from curing a composition of claim 9.

17. A process comprising copolymerization of
(A) from about 0.1 to about 50 percent by weight of at least one alkenylphenyl cyanate represented by formula I in the specification; and
(B) from about 1 to about 50 percent by weight of at least one polymerizable ethylenically unsaturated material in the presence of;
(C) from about 10 to about 99 percent by weight of at least one aromatic polycyanate or aromatic polycyanamide or mixture thereof represented by formulas II, III, IV or V in the specification wherein each A is independently a divalent hydrocarbon group having from 1 to about 10 carbon atoms, $$-O-, -\overset{O}{\underset{\parallel}{C}}-, -S-, -S-S-, -\overset{O}{\underset{\parallel}{S}}-, -\overset{O}{\underset{\underset{\parallel}{O}}{\overset{\parallel}{S}}}- \text{ or}$$

$$-O-\overset{O}{\underset{\parallel}{C}}-O-;$$

each A' is independently a divalent hydrocarbon group having from 1 to about 6 carbon atoms or a

[structure: bridged polycyclic group with subscript p]

group; p has a value of from zero to about 10; each R' is independently hydrogen, a hydrocarbyl or hydrocarbyloxy group having from 1 to about 10 carbon atoms; each Q is independently a —O—C≡N or $$-\underset{H}{\overset{|}{N}}-C\equiv N$$

group; each $Z^1$ is independently hydrogen, a hydrocarbyl or hydrocarbyloxy group having from 1 to about 6 carbon atoms, chlorine, bromine, a —O—C≡N group or a $$-\underset{H}{\overset{|}{N}}-C\equiv N$$

group; n has a value of zero or 1; n' has a value from zero to about 100; n" has a value of from about 0.001 to about 6; x has a value of 4 and x' has a value of 3; wherein the percent by weight of the components is based upon total weight of the components (A), (B) and (C).

18. A process of claim 17 wherein component (C) is an aromatic polycyanate or mixture of such polycyanates.

* * * * *